(12) United States Patent
Hashino et al.

(10) Patent No.: US 8,998,869 B2
(45) Date of Patent: Apr. 7, 2015

(54) PACKAGE STRUCTURE OF ABSORBENT ARTICLE AND METHOD OF MANUFACTURING PACKAGE STRUCTURE

(75) Inventors: Akira Hashino, Kagawa (JP); Yuki Noda, Kagawa (JP)

(73) Assignee: Unicharm Corporation, Ehime (JP)

( * ) Notice: Subject to any disclaimer, the term of this patent is extended or adjusted under 35 U.S.C. 154(b) by 329 days.

(21) Appl. No.: 13/577,071

(22) PCT Filed: Feb. 3, 2011

(86) PCT No.: PCT/JP2011/052265
§ 371 (c)(1),
(2), (4) Date: Oct. 17, 2012

(87) PCT Pub. No.: WO2011/096485
PCT Pub. Date: Aug. 11, 2011

(65) Prior Publication Data
US 2013/0030400 A1    Jan. 31, 2013

(30) Foreign Application Priority Data
Feb. 3, 2010   (JP) ................. 2010-022625

(51) Int. Cl.
*A61F 13/15* (2006.01)
*A61F 13/551* (2006.01)

(52) U.S. Cl.
CPC ....... *A61F 13/5514* (2013.01); *A61F 13/15747* (2013.01)

(58) Field of Classification Search
USPC ...................... 604/385.02, 385.04, 385.05
See application file for complete search history.

(56) References Cited

U.S. PATENT DOCUMENTS

| | | |
|---|---|---|
| 6,186,993 B1 | 2/2001 | Toyoshima et al. |
| 2003/0014032 A1 | 1/2003 | Kashiwagi et al. |
| 2003/0130642 A1 | 7/2003 | Kashiwagi et al. |
| 2007/0179466 A1 | 8/2007 | Tremblay et al. |

FOREIGN PATENT DOCUMENTS

| | | |
|---|---|---|
| CN | 1437920 A | 8/2003 |
| CN | 1157172 A | 7/2004 |
| CN | 1157172 C | 7/2004 |
| DE | 3806361 | 4/1989 |
| JP | H09-253127 A | 9/1997 |
| JP | H09-327478 A | 12/1997 |
| JP | H10-508548 A | 8/1998 |
| JP | 2000-5227 A | 1/2000 |

(Continued)

OTHER PUBLICATIONS

Official Action from corresponding Chinese Application No. 201180008026.5 dated Jan. 6, 2014 (14 pgs.).
Chinese Official Action from corresponding Chinese Application No. 201180008026.5 dated Jan. 6, 2014 (14 pgs).

(Continued)

*Primary Examiner* — Jacqueline F. Stephens
(74) *Attorney, Agent, or Firm* — Brinks Gilson & Lione

(57) ABSTRACT

A packaging medium is provided only on non-skin side surfaces of a third portion and a fourth portion. The length of the packaging medium in a lengthwise direction of a sanitary napkin is shorter than the length of the sanitary napkin. A second portion includes a folded end portion which is formed by a first folded portion provided on a side of a first portion of the sanitary napkin which opposes a first folding portion. The folded end portion is folded over a non-skin side surface of the second portion.

5 Claims, 11 Drawing Sheets

(56) References Cited

FOREIGN PATENT DOCUMENTS

| | | |
|---|---|---|
| JP | 2000-083991 | 3/2000 |
| JP | 2003-24373 A | 1/2003 |
| JP | 2006-180989 A | 7/2006 |
| JP | 2006-180990 A | 7/2006 |
| JP | 2011-136099 A | 7/2011 |
| WO | WO 2007/041210 A1 | 4/2007 |

OTHER PUBLICATIONS

European Search Report from corresponding European Application No. 11739833.9 dated Oct. 15, 2013 (6 pgs).
Japanese Official Official Action from corresponding Japanese Application No. 2010-022625 (8 pgs), Apr. 30, 2014.
Eurasian Official Action and translation from corresponding Eurasian Application No. 201201075 dated Jul. 2, 2014 (4 pgs).
Japanese Office Action and translation from corresponding Japanese Application No. 2010-022625 (6 pgs), Apr. 30, 2014.

FIG. 3
(a)
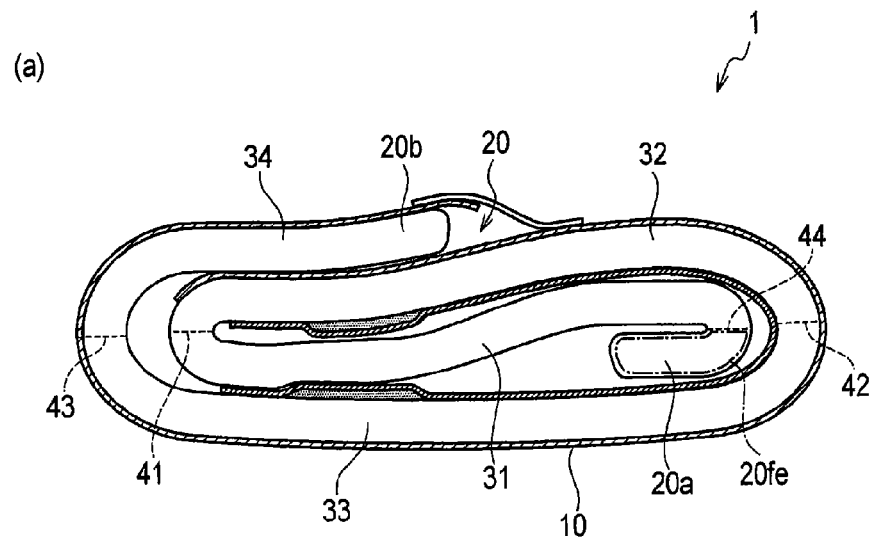
(b)
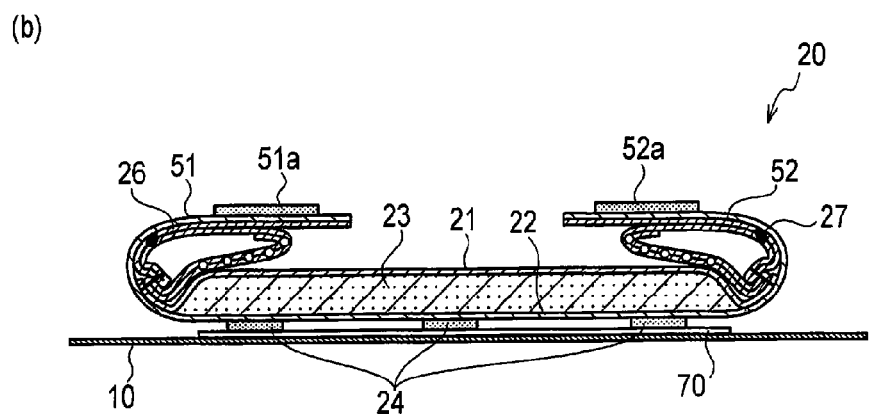

PACKAGE STRUCTURE OF ABSORBENT ARTICLE AND METHOD OF MANUFACTURING PACKAGE STRUCTURE

RELATED APPLICATION

This application is a 35 U.S.C. §371 national phase filing of International Patent Application No. PCT/JP2011/052265 filed Feb. 3, 2011, to which priority is claimed under 35 U.S.C. §120 and through which priority is claimed under 35 U.S.C. §119 to Japanese Patent Application No. 2010-022625, filed Feb. 3, 2010.

TECHNICAL FIELD

The present invention relates to a package structure of an absorbent article formed by folding the absorbent article and a packaging medium several times altogether, and to a method of manufacturing the package structure.

BACKGROUND ART

From a hygiene standpoint, absorbent articles, such as sanitary napkins, are typically packaged individually with a sheet-like packaging medium. Absorbent articles with elongated product length to provide sufficient absorbency while a wearer is, for example, sleeping are used widely. Such absorbent articles with elongated product length are typically folded into four while normal products are folded into three (for example, Patent Document 1).

For package structures of such absorbent articles (hereinafter, sometimes simply referred to as "packaged product(s)"), methods of saving packaging media and thereby reducing the manufacturing cost have been known. First, for example, an absorbent article is folded from one side, in a lengthwise direction, and is disposed on a packaging medium with the folded side facing downward. Then, the absorbent article is folded from the other side toward the one side together with the packaging medium to be joined to the one side. The folded absorbent article has a Z-shaped side configuration. Such a packaged product has been disclosed (see Patent Document 2). With such a packaged product, a required amount of the packaging medium is reduced as compared with a case in which the packaging medium is provided on an entire back surface of the absorbent article.

RELATED ART DOCUMENT

Patent Document

[Patent Document 1]
   Japanese Patent No. 3685935 (pages 3 and 4 and FIG. 2)
[Patent Document 2]
   Japanese Unexamined Patent Application Publication No. 2003-24373 (pages 3 and 4 and FIGS. 2 and 3)

SUMMARY OF INVENTION

In manufacturing steps of packaged products, in a case in which packaged products are manufactured by disposing absorbent articles on a sheet constituted by packaging media continuously arranged such that the lengthwise direction of the absorbent articles are perpendicular to a conveyance direction and then folding the absorbent articles, if the length of the packaging media in a widthwise direction perpendicular to the conveyance direction is shorter than the length of the absorbent articles for the reduction in the required amount of the packaging media, the following problem may arise.

That is, since one end portion in the lengthwise direction of the absorbent article from a side end of the packaging medium is not joined to the packaging medium, when the one end portion which is already folded once is to be folded again in a related art folding device incorporating a folding plate, such as a sailor, the one end portion which had been folded may be unfolded. As a result, the absorbent article sometimes cannot be folded successfully. Such a problem is not caused if the absorbent article is disposed on the packaging medium with one end portion in the lengthwise direction thereof being folded in advance even if the length of the packaging medium is shorter than the length of the absorbent article. However, disposing (i.e., transferring) such an absorbent article with the one end portion folded in advance on the packaging medium may cause other problems, such as complexity in a structure of an apparatus for manufacturing the packaged product.

The present invention has been made in view of these circumstances, and an object thereof is to provide a package structure of an absorbent article capable of folding the absorbent article reliably while saving a required amount of a packaging medium even if the absorbent article is folded after being disposed on the packaging medium, and a method of manufacturing the package structure.

In order to achieve the above-described object, the present invention has the following features. In summary, a package structure (a packaged product 1) of an absorbent article which includes the absorbent article (a sanitary napkin 20) and a sheet-like packaging medium (a packaging medium 10) which individually packages the absorbent article, the absorbent article having a skin side surface (a topsheet 21) located on a side of a wearer's skin and a non-skin side surface (a backsheet 22) located on a side of underwear of a wearer, the absorbent article having a lengthwise direction (a lengthwise direction L) and a widthwise direction (a widthwise direction W) perpendicular to the lengthwise direction, and the absorbent article and the packaging medium being integrally folded in the lengthwise direction, wherein: the absorbent article at least comprises a first portion (a first portion 20a) which includes an end portion of the absorbent article, a second portion (a second portion 31) which is disposed adjacent to the first portion via a first folded portion (a first folded portion 44), a third portion (a third portion 32) which is disposed adjacent to the second portion via a second folded portion (a second folded portion 41) and a fourth portion (a fourth portion 33) which is disposed adjacent to the third portion via a third folded portion (a third folded portion 42); the first portion is folded on a side of a non-skin side surface of the second portion via the first folded portion; the third portion is folded on a side of a skin side surface of the second portion via the second folded portion; the fourth portion is folded on the side of the non-skin side surface of the second portion via the third folded portion; and the packaging medium is joined at least partially to the third portion and the fourth portion and not joined to the first portion and the second portion.

Another feature of the present invention is, in summary, a method of manufacturing a package structure of an absorbent article which includes an absorbent article and a sheet-like packaging medium which individually packages the absorbent article using a device for manufacturing, in which the absorbent article has a skin side surface located on a side of a wearer's skin and a non-skin side surface located on a side of underwear of a wearer, the absorbent article has a lengthwise direction and a widthwise direction perpendicular to the lengthwise direction, and the device for manufacturing includes a conveyor which conveys the absorbent article in a conveyance direction and a circular belt provided to come close to the conveyor as it approaches a downstream of the conveyance direction, the method of manufacturing the package structure including: a disposing step in which the absorbent article is disposed on the packaging medium which is successively conveyed by the conveyor in the conveyance direction such that the lengthwise direction of the absorbent article corresponds to a direction perpendicular to the conveyance direction; a folding step in which one end portion in the lengthwise direction of the absorbent article conveyed together with the packaging medium is brought into contact with a folding plate and thereby folded to be substantially vertical to the conveyance direction and the direction perpendicular to the conveyance direction; and a folding over step in which the one end portion in the lengthwise direction of the absorbent article is folded on a side of the skin side surface of the absorbent article by bringing the circular belt into contact with the non-skin side surface of the one end portion in the lengthwise direction of the absorbent article.

According to the features of the present invention, a package structure of an absorbent article in which the absorbent article is packaged reliably while saving a required amount of a packaging medium and a method of manufacturing the package structure can be provided.

BRIEF DESCRIPTION OF DRAWINGS

FIG. 3 (*a*) is a schematic lengthwise sectional view of the packaged product 1 through section F3A-F3A of FIG. 1 and FIG. 3 (*b*) a schematic widthwise sectional view of a sanitary napkin 20 through section F3B-F3B of FIG. 2(*a*).

DESCRIPTION OF EMBODIMENTS

Figure 1:
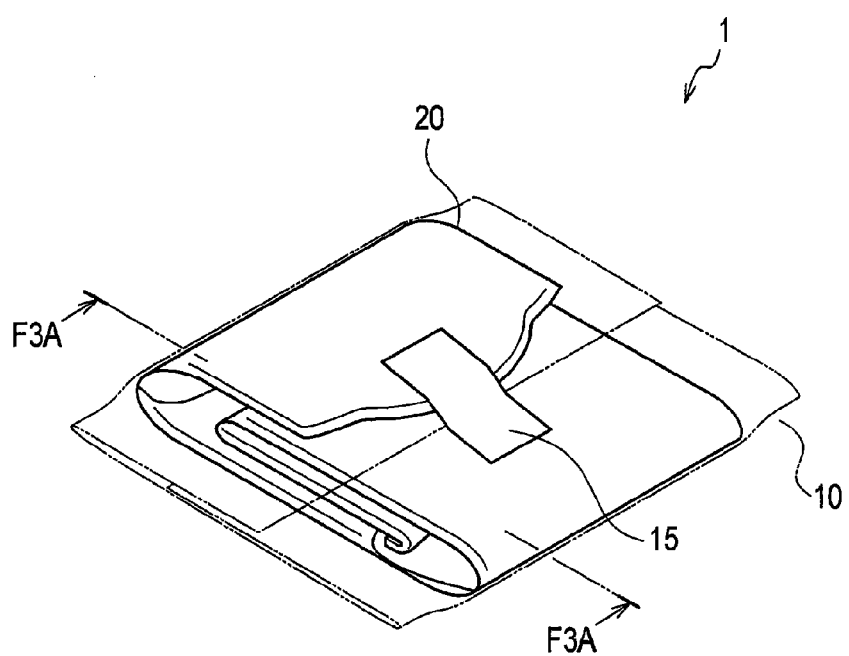
FIG. 1 is a schematic perspective view of an entire package structure 1 of an absorbent article according to an embodiment of the present invention.

Next, embodiments of a package structure of an absorbent article and a method of manufacturing the package structure according to the present invention will be described with reference to the drawings. In the description of the drawings below, the same or similar components are denoted by the same or similar reference numerals. It should be noted, however, that the drawings are schematic only and not to scale regarding, for example, dimensional ratios.

Accordingly, specific dimensions, for example, should be determined in consideration of the description below. It should also be noted that dimensional relationships and ratios may vary among different drawings.

(1) Schematic Structure of Entire Package Structure of Absorbent Article

FIG. 1 is a schematic perspective view of an entire package structure 1 of an absorbent article (hereinafter, referred to as a "packaged product 1") according to an embodiment of the present invention. As illustrated in FIG. 1, the packaged product 1 is constituted by a packaging medium 10, a locking tape 15 and a sanitary napkin 20. The packaged product 1 is formed by the packaging medium 10 and the sanitary napkin 20 which are folded together several times. In this embodiment, the sanitary napkin 20 constitutes the absorbent article.

The packaging medium 10 packages the sanitary napkin 20 to prevent adhesion of foreign substances, such as dust, to the sanitary napkin 20. The packaging medium 10 is a sheet-like member which is brought into contact with a non-skin side surface, i.e., a backsheet 22, of the sanitary napkin 20 (not illustrated in FIG. 1; see FIG. 3(*b*)). The packaging medium 10 is folded together with the sanitary napkin 20. The packaging medium 10 may be formed of, for example, a film consisting of polypropylene, polyester, polyethylene, polyvinyl alcohol and composite materials thereof. Both side ends in a widthwise direction W (see FIG. 2(*a*)) of the folded packaging medium 10 are joined by, for example, heat sealing.

The sanitary napkin 20 is folded several times together with the packaging medium 10. The sanitary napkin 20 has a longitudinally elongated shape when developed from the folded state. The sanitary napkin 20 has an elongated product length as compared with normal products to provide sufficient absorbency while a wearer is, for example, sleeping. For this reason, the sanitary napkin 20 is folded into four in the lengthwise direction L of the product (not illustrated in FIG. 1; see FIG. 2) while normal products are folded into three.

The locking tape 15 is provided on the packaging medium 10 which packages the sanitary napkin 20 which is folded into four. The locking tape 15 can be held by a user when the user opens the packaged product 1.

Figure 2:
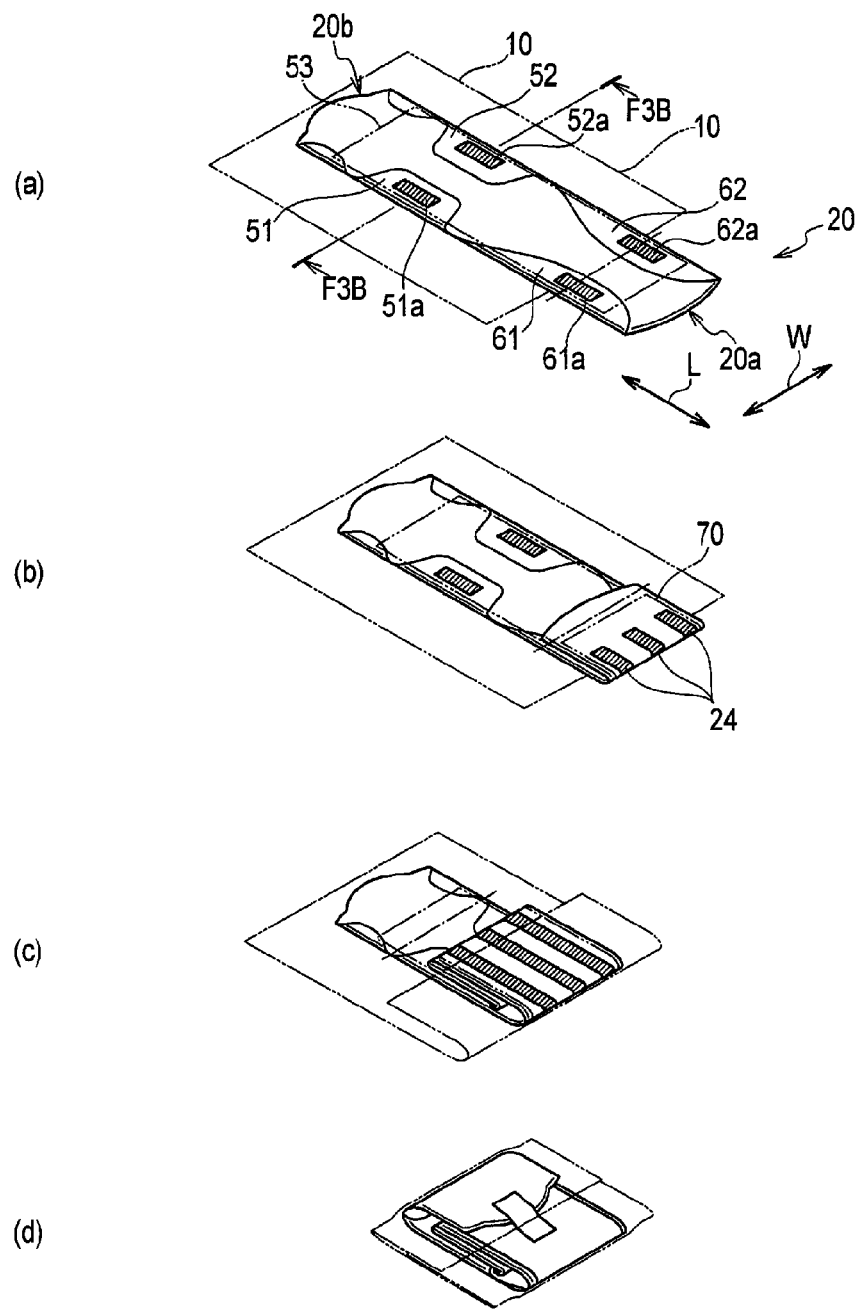
FIG. 2 (*a*) to 2 (*d*) schematically illustrates a configuration and a folding structure of the packaged product 1 according to the embodiment of the present invention.

FIGS. 2(*a*) to 2(*d*) schematically illustrate a configuration and a folding structure of the packaged product 1. As illustrated in FIGS. 2(*a*) to 2(*d*), the packaged product 1 is folded twice from a side of a first portion 20*a* in the lengthwise direction L and then folded once from a side of an end portion 20*b* in the lengthwise direction L to be folded into four.

The sanitary napkin 20 is provided with a pair of wings (i.e., a wing 51 and a wing 52) and a pair of hip flaps (i.e., a hip flap 61 and a hip flap 62). Thus, the sanitary napkin 20 has a longitudinally elongated shape in a state in which it is developed and has the lengthwise direction L and the widthwise direction W.

The wing 51 and the wing 52 extend outward in the widthwise direction W of the sanitary napkin 20 in a state in which they are developed and are folded over and fixed to a non-skin side of a crotch portion of underwear (not illustrated). The wing 51 and the wing 52 are folded over a side of a topsheet 21 of the sanitary napkin 20 (see FIG. 3(b)) in a state in which the sanitary napkin 20 is packaged.

The wing 51 (wing 52) includes a wing adhesive portion 51a (wing adhesive portion 52a) formed on a contact surface with the underwear. The wing adhesive portion 51a and the wing adhesive portion 52a may be formed of, for example, a hot-melt adhesive member consisting of styrene polymer, a tackifier and a plasticizer. When being folded, the wing 51 and the wing 52 are provided with an integrated wing release paper 53 which is removably attached to the wing adhesive portion 51a and the wing adhesive portion 52a. The wing release paper 53 may be formed of, for example, a paper material having a releasing layer of, for example, silicon resin.

Like the wing 51 and the wing 52, the hip flap 61 and the hip flap 62 extend outward in the widthwise direction W of the sanitary napkin 20 in a state in which they are developed. The hip flap 61 and the hip flap 62 are located further toward the wearer's buttock than the wing 51 and the wing 52 and are fixed to a skin contact surface of the underwear. The hip flap 61 and the hip flap 62 are also folded over a side of the topsheet 21 of the sanitary napkin 20 in a state in which the sanitary napkin 20 is packaged.

The hip flap 61 (hip flap 62) includes a flap adhesive portion 61a (flap adhesive portion 62a) formed on the contact surface with the underwear. The flap adhesive portion 61a and the flap adhesive portion 62a may be formed of the same material as those of the wing adhesive portion 51a and the wing adhesive portion 52a.

FIG. 3(a) is a schematic lengthwise sectional view of the packaged product 1 through section F3A-F3A of FIG. 1. In FIG. 3(a), hatching is partially omitted.

As illustrated in FIG. 3(a), the packaged product 1 at least includes the first portion 20a for packaging an end portion of the packaged product 1, a second portion 31 disposed adjacent to the first portion 20a via a first folded portion 44, a third portion 32 disposed adjacent to the second portion 31 via a second folded portion 41 and a fourth portion 33 disposed adjacent to the third portion 32 via a third folded portion 42.

The first portion 20a is folded on a side of a non-skin side surface of the second portion 31 via the first folded portion 44. The third portion 32 is folded on a side of a skin side surface of the second portion 31 via the second folded portion 41. The fourth portion 33 is folded on a side of a non-skin side surface of the second portion 31 via the third folded portion 42. A fifth portion 34 is folded on a side of a non-skin side surface of the third portion 32 via the fourth folded portion 43. The packaging medium 10 is joined at least partially to the third portion 32 and the fourth portion 33 and is not joined to the first portion 20a and the second portion 31.

FIG. 3(b) is a schematic widthwise sectional view of the sanitary napkin 20 through section F3B-F3B of FIG. 2(a). As illustrated in FIG. 3(b), the sanitary napkin 20 includes a topsheet 21 which forms a skin side surface located on a side of the wearer's skin, and a backsheet 22 which forms a non-skin side surface located on a side of the wearer's underwear. An absorber 23 which absorbs, for example, wearer's bodily fluids is provided between the topsheet 21 and the backsheet 22.

The topsheet 21 is formed of nonwoven fabric. Materials of the topsheet 21 are not particularly limited as long as they are sheet-like materials through which liquids pass, such as a perforated plastic sheet. The backsheet 22 is formed of a film mainly consisting of, for example, polyethylene or polypropylene, a perforated resin film, and a sheet in which a perforated resin film is joined to nonwoven fabric, such as spunbond or spunlace.

The absorber 23 is formed by a material including hydrophilic fibers and pulp. Examples of the hydrophilic fibers may include ground pulp, cellulose, such as cotton, regenerated cellulose, such as rayon and fabric rayon, semi-synthetic cellulose, such as acetate and triacetate, particulate polymer, fibrous polymer, thermoplastic hydrophobic chemical fibers and thermoplastic hydrophobic chemical fibers subject to a hydrophilic treatment. The hydrophilic fibers can be used alone or in combination thereof.

As illustrated in FIG. 2(a) or 3(b), the sanitary napkin 20 includes a back surface adhesive portion 24. The back surface adhesive portion 24 is formed on a backside, i.e., the back surface 22, of the sanitary napkin 20. The back surface adhesive portion 24 may be formed of the same material as that of, for example, the wing adhesive portion 51a. A main body release paper 70 removably attached to the back surface adhesive portion 24 is provided on the backsheet 22. The main body release paper 70 may be formed of the same material as that of, for example, the wing release paper 53.

As illustrated in FIG. 3(b), the sanitary napkin 20 includes a pair of leakage-preventing portions (a leakage-preventing portion 26 and a leakage-preventing portion 27). The leakage-preventing portion 26 and the leakage-preventing portion 27 are formed of nonwoven fabric and elastic yarn (for example, polyurethane elastic yarn).

The sanitary napkin 20 may be manufactured using the material disclosed in the above-described Patent Document 2, for example.

(2) Method of Manufacturing Packaged Product

Figure 5:
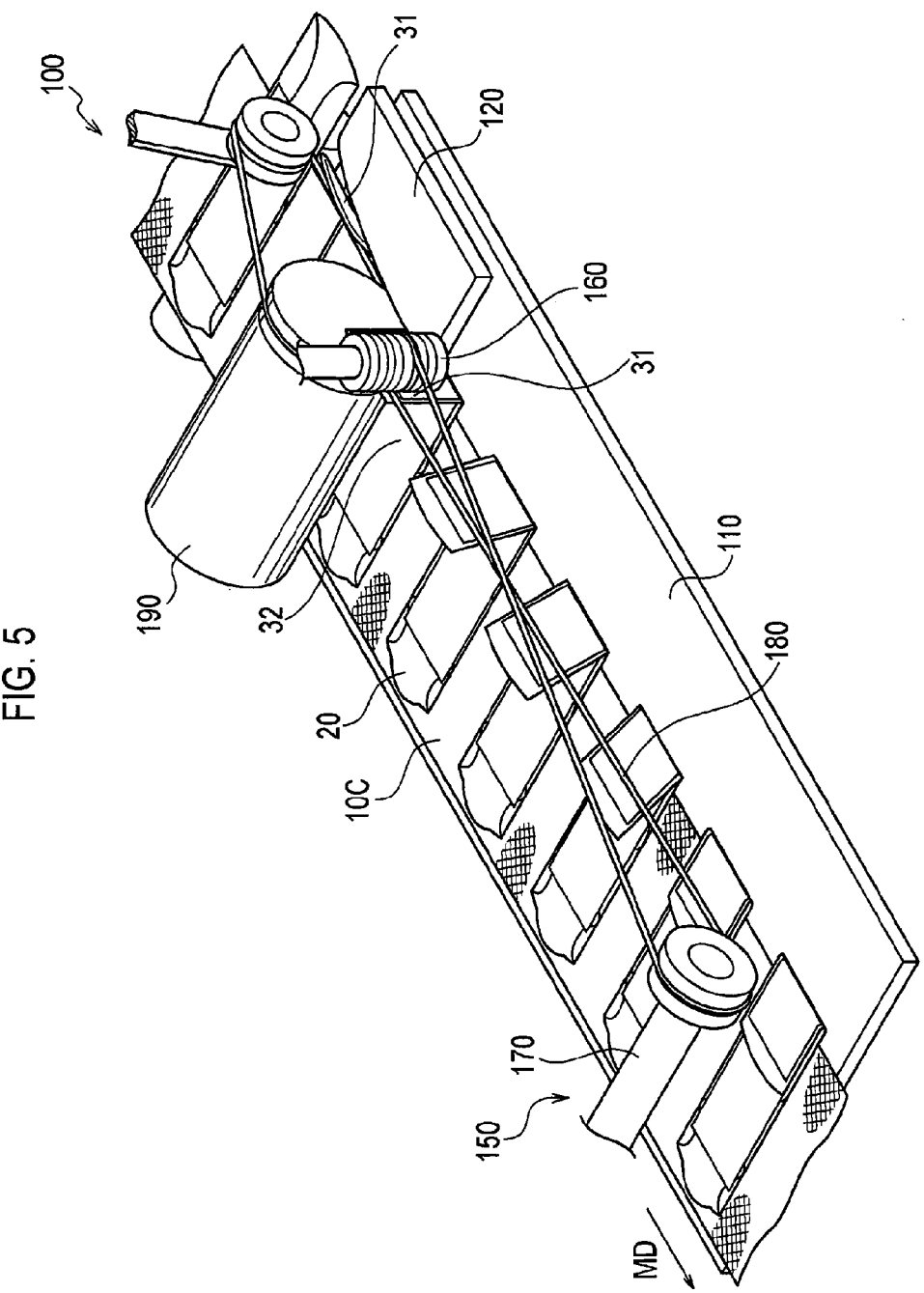
FIG. 5 is a perspective view of a folding device 100 used in a manufacturing process (first folding step) of the packaged product 1 according to the embodiment of the present invention.
Figure 6:
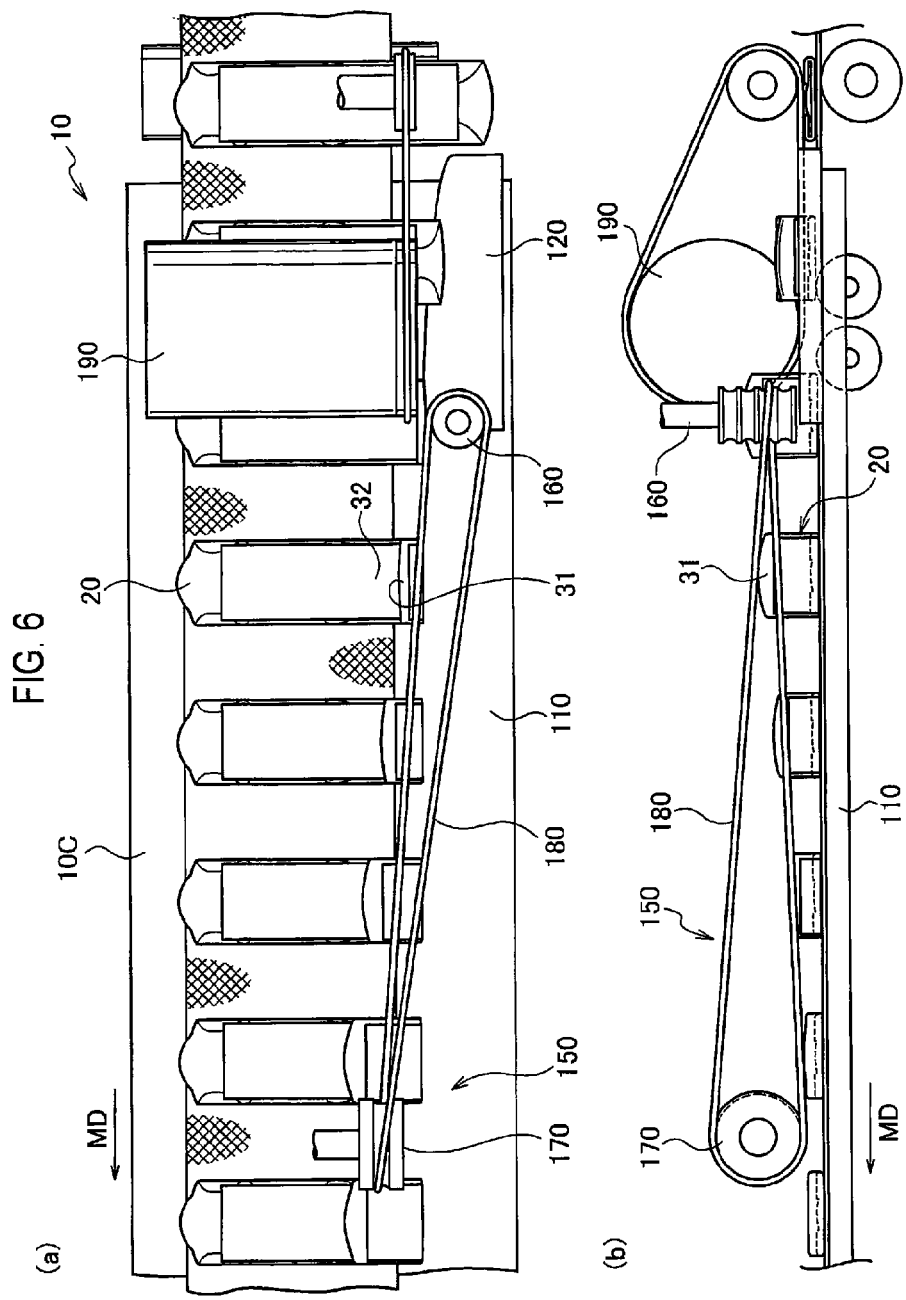
FIGS. 6 (*a*) and 6(*b*) is a plan view and a side view of the folding device 100 according to the embodiment of the present invention.
Figure 7:
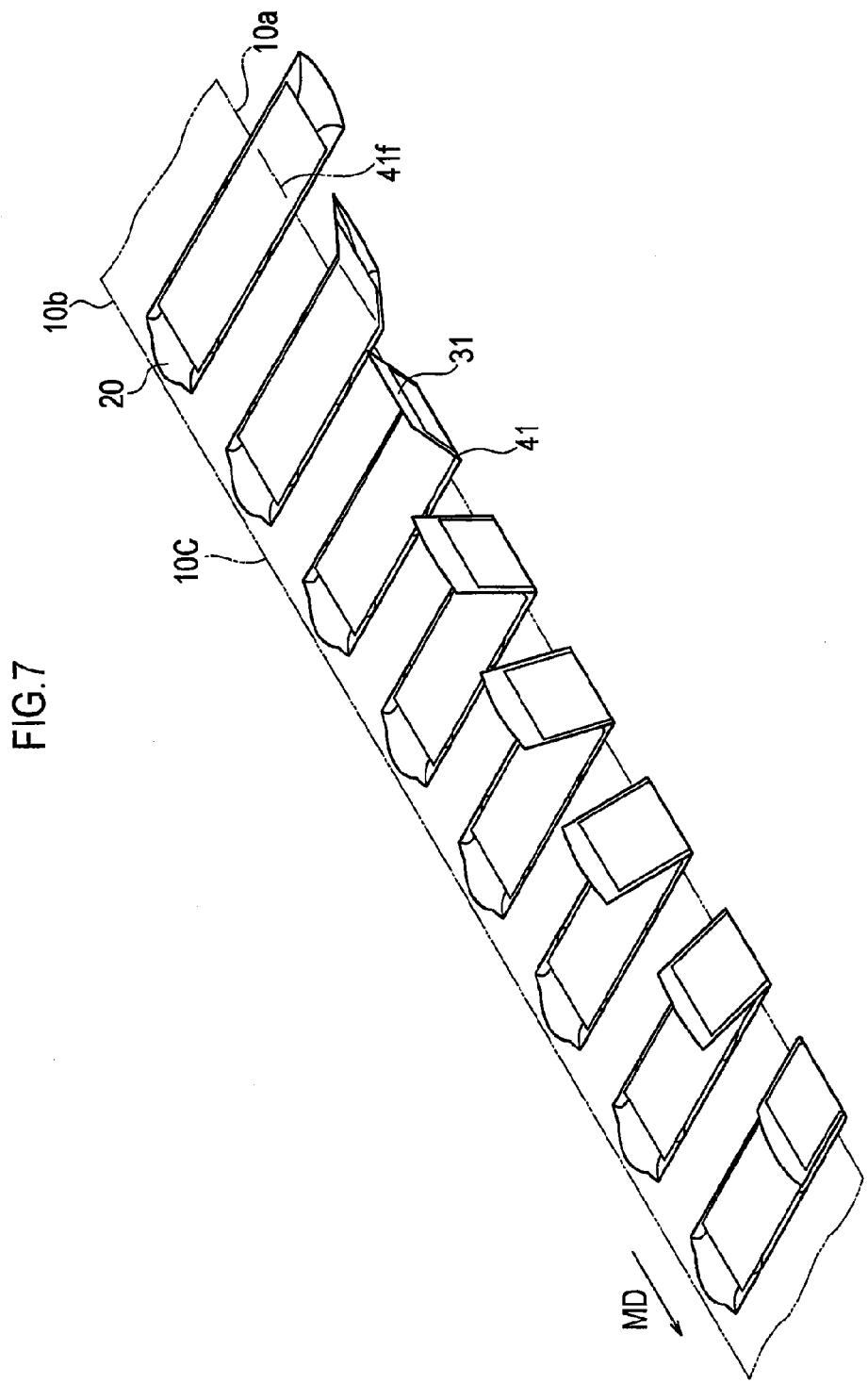
FIG. 7 illustrates changes in shape of the sanitary napkin 20 which is being folded by the folding device 100 according to the embodiment of the present invention.

Next, a method of manufacturing the packaged product 1 will be described with reference to FIGS. 4 to 10. FIGS. 4(a) to 4(d) schematically illustrate a manufacturing process of the packaged product 1. FIG. 5 is a perspective view of a folding device 100 used in a manufacturing process (first folding step) of the packaged product 1 and FIGS. 6(a) and 6(b) are a plan view and a side view of the folding device 100. FIG. 7 illustrates changes in shape of the sanitary napkin 20 folded by the folding device 100.

Figure 8:
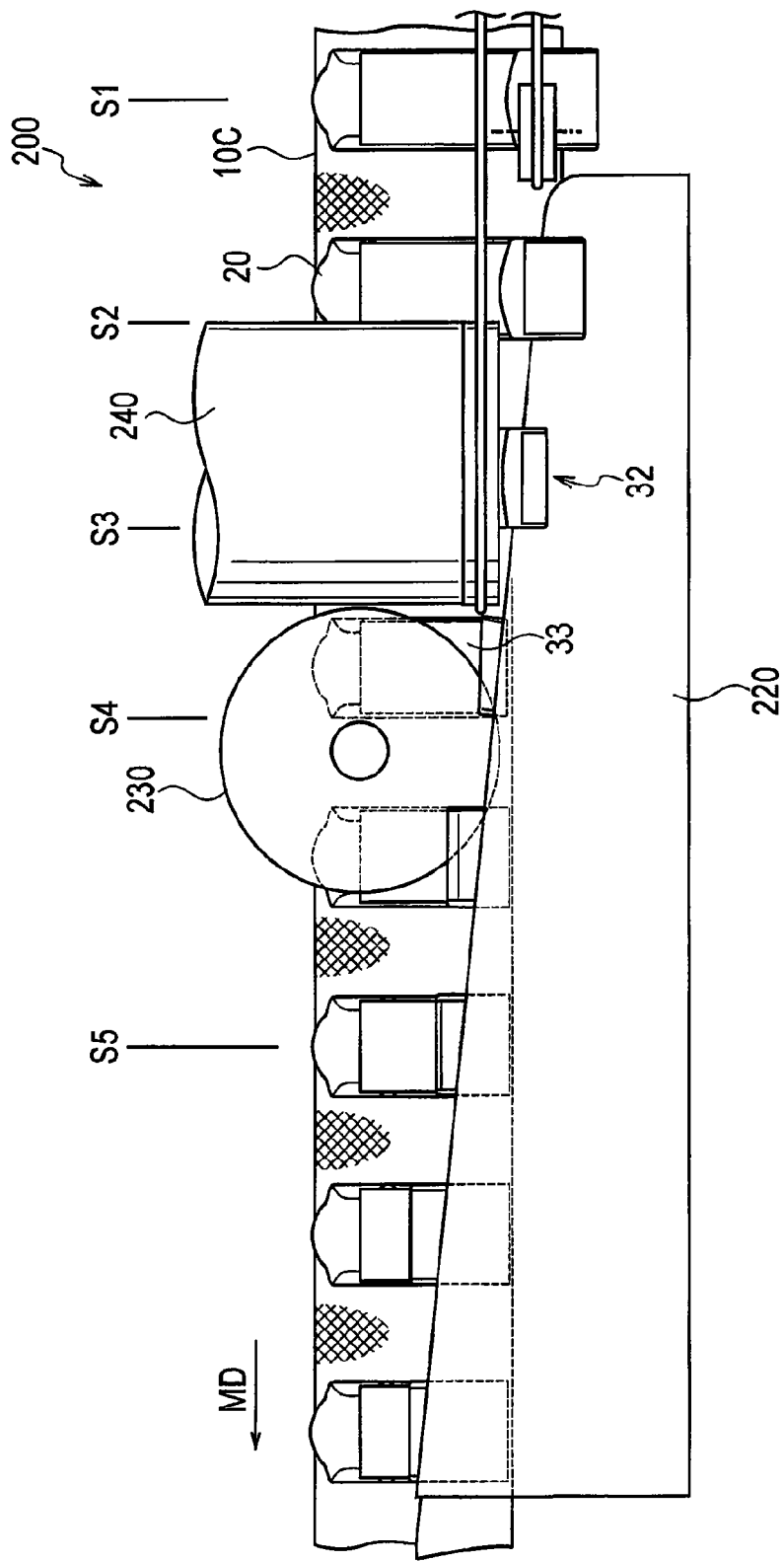
FIG. 8 is a plan view of a folding device 200 used in the manufacturing process (second folding step) of the packaged product 1 according to the embodiment of the present invention.

FIG. 8 is a plan view of a folding device 200 used in the manufacturing process (second folding step) of the packaged product 1. FIGS. 9(a) to 9(e) illustrate formation of a folded end portion 20fe in the second portion 31 by the folding device 200. FIG. 10 illustrates change in shape of the sanitary napkin 20 folded by the folding device 200. Hereafter, a disposing step, the first folding step, the second folding step and a third folding step will be described.

(2.1) Disposing Step

As illustrated in FIGS. 4(a) and 7, the packaging media 10 are continuously disposed in a conveyance direction MD of the packaging media 10 and constitute a continuous sheet 10C. In the disposing step, the sanitary napkins 20 are disposed on the continuously disposed packaging media 10 such that the lengthwise direction L of the sanitary napkins 20 is perpendicular to the conveyance direction MD. In this manner, the sanitary napkins 20 are disposed at equal spaces on the continuous sheet 10C.

In the disposing step, each of the sanitary napkins 20 is disposed on the packaging medium 10 such that one side in the lengthwise direction L of the sanitary napkin 20 extends further outward than a side end 10a in the widthwise direction W of each packaging medium 10 disposed perpendicular to the conveyance direction MD. That is, the packaging medium 10 is joined to at least partially to the third portion 32 and the fourth portion 33, and not joined to the first portion 20a and the second portion 31. The packaging medium 10 is not provided on the non-skin side surface of the second portion 31, but is provided only on the non-skin side surface of the third portion 32, on the non-skin side surface of the fourth portion 33 and on the non-skin side surface of the fifth portion 34.

The sanitary napkins 20 are disposed on the continuous sheet 10C such that the fifth portions 34 are located further inward in the widthwise direction than the other end portion 10*b* in the widthwise direction of the packaging medium 10. The length of the packaging medium 10 along the lengthwise direction L is shorter than the length of the sanitary napkin 20 along the lengthwise direction L. Thus, the amount of the packaging medium 10 required to package the sanitary napkin 20 is saved.

At the time the sanitary napkin 20 is disposed on the continuous sheet 10C, the wing adhesive portion 51*a*, the wing adhesive portion 52*a* and the back surface adhesive portion 24 are formed on the sanitary napkin 20. At the time the sanitary napkin 20 is disposed on the continuous sheet 10C, the wing release paper 53 and the main body release paper 70 are also provided in the sanitary napkin 20.

(2.2) Folding Step

In a folding step, the sanitary napkin 20 disposed on the packaging medium 10 is folded several times. In this embodiment, the packaged product 1 constituted by the sanitary napkin 20 which is folded into four is formed through a first folding step to a third folding step.

(2.2.1) First Folding Step

Figure 4:
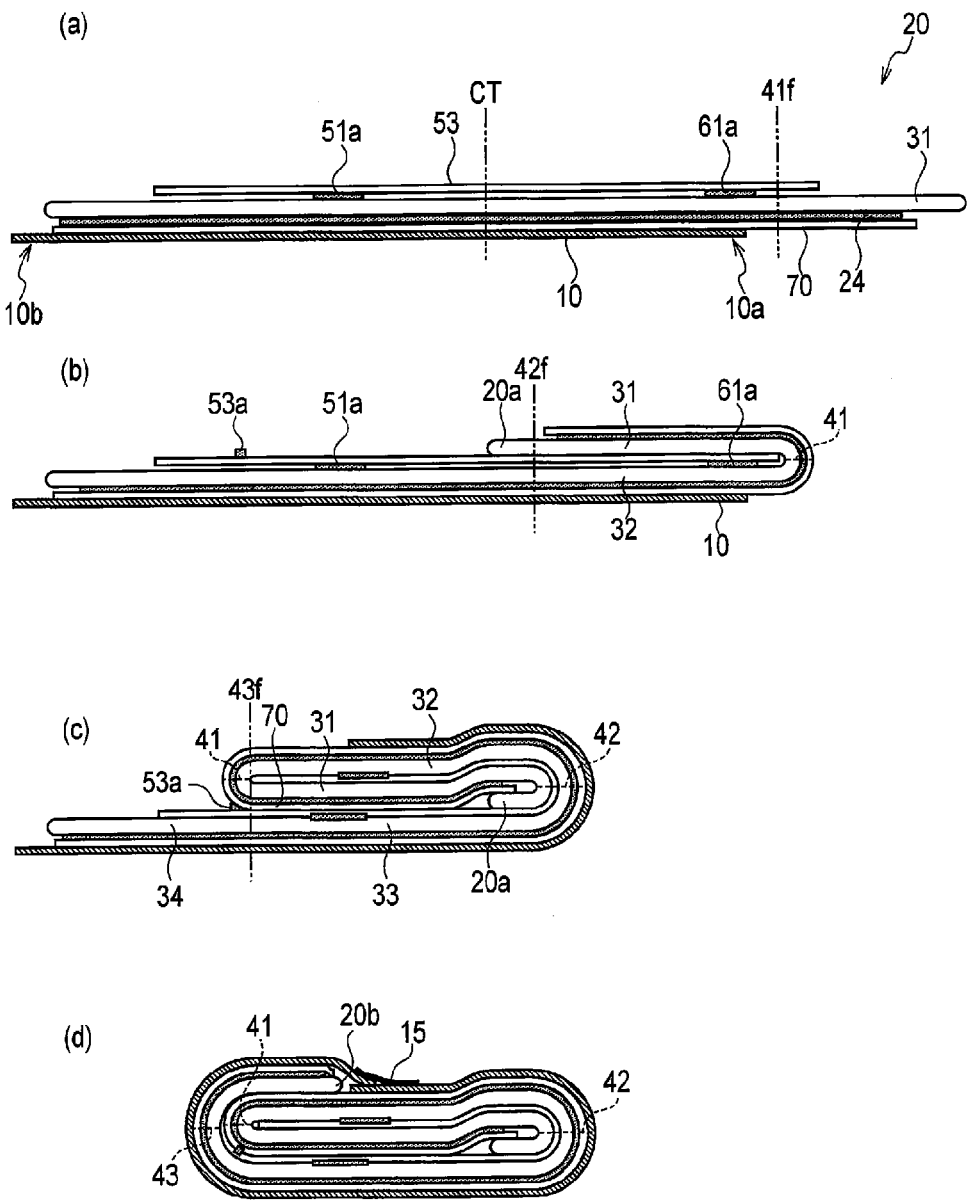
FIGS. 4 (*a*) to 4(*d*) schematically illustrates a manufacturing process of the packaged product 1 according to the embodiment of the present invention.

As illustrated in FIGS. 4(*a*), 4(*b*) and 7, in the first folding step, one end in the lengthwise direction L of the sanitary napkin 20 is folded over the skin side surface of the other side of the sanitary napkin 20 along a first folding line 41*f* extending in the widthwise direction W of the sanitary napkin 20. In this embodiment, in a state in which the sanitary napkin 20 is developed, the first folding line 41*f* is located further toward the second portion 31 than a center CT in the lengthwise direction of the sanitary napkin 20.

In the first folding step, one side (i.e., the first portion 20*a*) in the lengthwise direction L of the sanitary napkin 20 in which the packaging medium 10 is not provided on the non-skin side surface of the second portion 31 is folded over the skin side surface of the other side (i.e., the end portion 20*b*). Thus, as illustrated in FIG. 4(*b*), the second portion 31 is independently folded in the first folding portion 41 over the skin side surface of the third portion 32 not together with the packaging medium 10.

In the first folding step, the folding device 100 illustrated in FIGS. 5 to 7 is used. The folding device 100 is provided with a conveyor 110, a folding plate 120, an eight shaped belt mechanism 150 and a pressing roller 190.

The conveyor 110 conveys the continuous sheet 10C on which the sanitary napkins 20 are disposed at equal spaces. The folding plate 120 abuts the second portion 31 of the sanitary napkin 20 conveyed by the conveyor 110 and raises the second portion 31 substantially upright with respect to the skin side surface of the third portion 32. In particular, the folding plate 120 has a configuration such that its distance from the pressing roller 190 becomes smaller as it approaches the downstream of the conveyance direction MD. Portions other than the second portion 31 of the sanitary napkin 20 are pressed down by the pressing roller 190, and the second portion 31 is folded by the folding plate 120 in a gap formed between the folding plate 120 and a side surface of the pressing roller 190.

The eight shaped belt mechanism 150 includes a vertical roller 160, a horizontal roller 170 and an circular belt 180. The vertical roller 160 has an axial center along a vertical direction with respect to the skin side surface at the other side (i.e., the end portion 20*b*) of the sanitary napkin 20. The horizontal roller 170 has an axial center parallel to the skin side surface at the other side of the sanitary napkin 20 and is perpendicular to the conveyance direction MD.

The vertical roller 160 is provided such that the skin side surface of the second portion 31 which is raised upright by the folding plate 120 and the circular belt 180 are brought into contact with each other. In particular, the vertical roller 160 is located at a side of the second portion 31 which is raised upright. A plurality of channels in accordance with the width of the circular belt 180 are formed in a peripheral portion of the vertical roller 160. The channel to which the circular belt 180 is guided can be suitably changed in accordance with, for example, a physical relationship with the sanitary napkin 20.

The horizontal roller 170 is located above the skin side surface of the other side of the sanitary napkin 20 in the downstream of the conveyance direction MD than the vertical roller 160 and at a position at which the circular belt 180 presses down the one non-skin side surface of the sanitary napkin 20.

The circular belt 180 is wound around the peripheral portion of the vertical roller 160 and a peripheral portion of the horizontal roller 170 in a crossed manner to form a figure-of-eight shape. The circular belt 180 is rotated in accordance with a conveyance velocity of the sanitary napkins 20. The circular belt 180 is moved in contact with the non-skin side surface of the second portion 31 which is raised substantially vertical with respect to the skin side surface of the other side of the sanitary napkin 20, and the second portion 31 is folded over the skin side surface of the other side of the sanitary napkin 20.

That is, when seen from a direction perpendicular to the skin side surface of the other side of the sanitary napkin 20, the circular belt 180 is moved from the one side toward the other side of the sanitary napkin 20 as it approaches to the downstream of the conveyance direction MD, and when seen from a widthwise direction of the packaging medium 10, the circular belt 180 comes close to the skin side surface of the other side of the sanitary napkin 20 as it approaches the downstream of the conveyance direction MD.

(2.2.2) Second Folding Step

As illustrated in FIGS. 4(*b*), 4(*c*) and 10, in the second folding step, the second portion 31 and the third portion 32 are folded together with the packaging medium 10 over the skin side surface of the other side of the sanitary napkin 20 which does not overlap the folded portion. The second portion 31 is a folded portion which includes one side (i.e., the first portion 20*a*) of the sanitary napkin 20 folded in the first folding step along the second folding line 42*f* extending in the widthwise direction W. The third portion 32 is a portion of the other side of the sanitary napkin 20 which overlaps the folded portion. That is, the third portion 32 over which the second portion 31 is folded is folded over the skin side surface of the fourth portion 33 together with the packaging medium 10 in a second folding portion 42.

In this embodiment, the second folding line 42*f* is provided further toward the first folding line 41*f* (i.e., the first folding portion 41) than the first portion 20*a* of the sanitary napkin 20. In a state in which only the second portion 31 is folded, the second folding line 42*f* is located further toward the first folding portion 41 than at two-thirds of the entire length in the lengthwise direction of the sanitary napkin 20. That is, the first portion 20*a* of the one side of the sanitary napkin 20 folded in the first folding step is folded together with the second portion 31 at the position of the second folding line 42f. In this manner, as illustrated in FIGS. 3(a) and 9(b) to 9(e), the folded end portion 20fe is formed.

Figure 9:
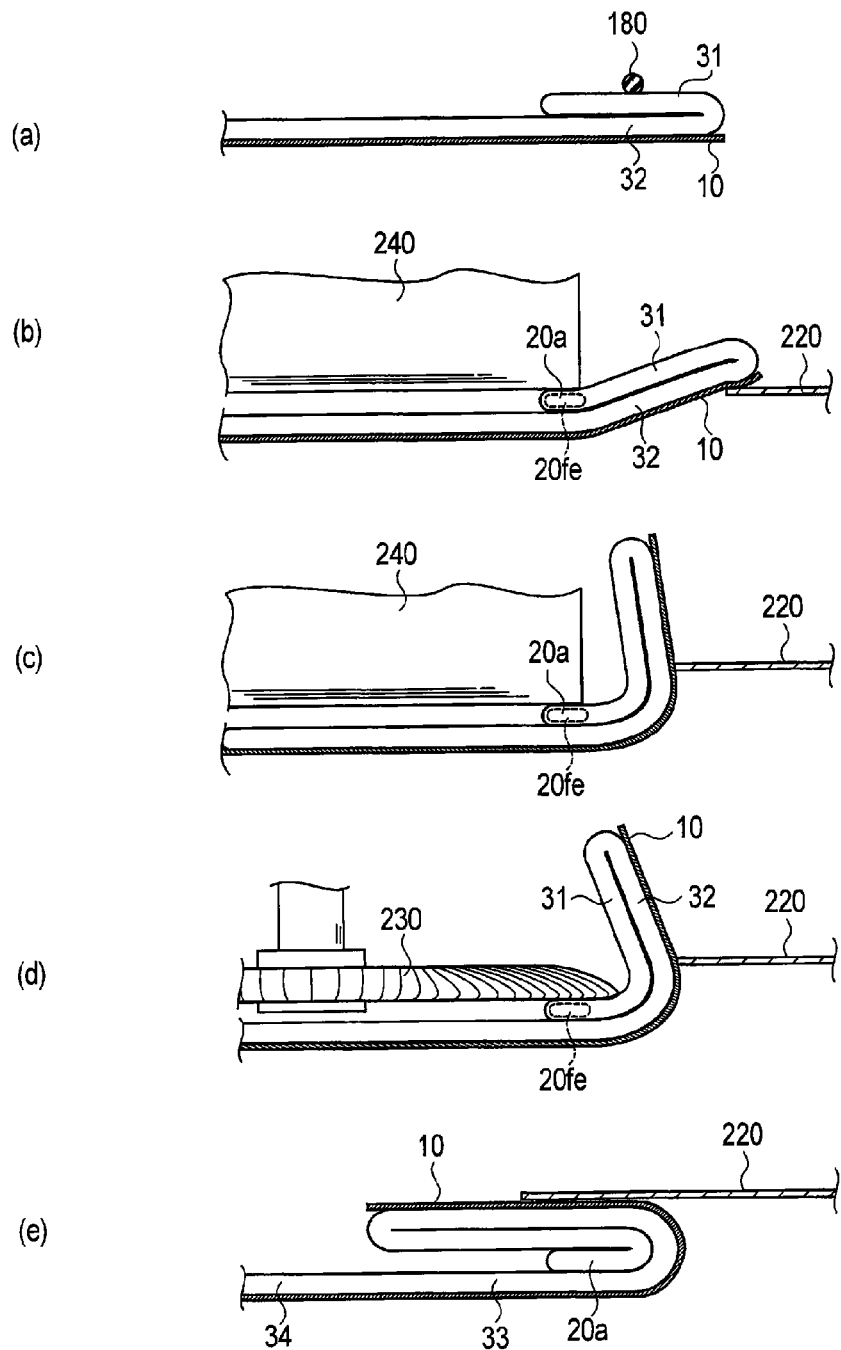
FIGS. 9(*a*) to 9(*e*) illustrate formation of a folded end portion 20*fe* in a second portion 31 by the folding device 200 according to the embodiment of the present invention.
Figure 10:
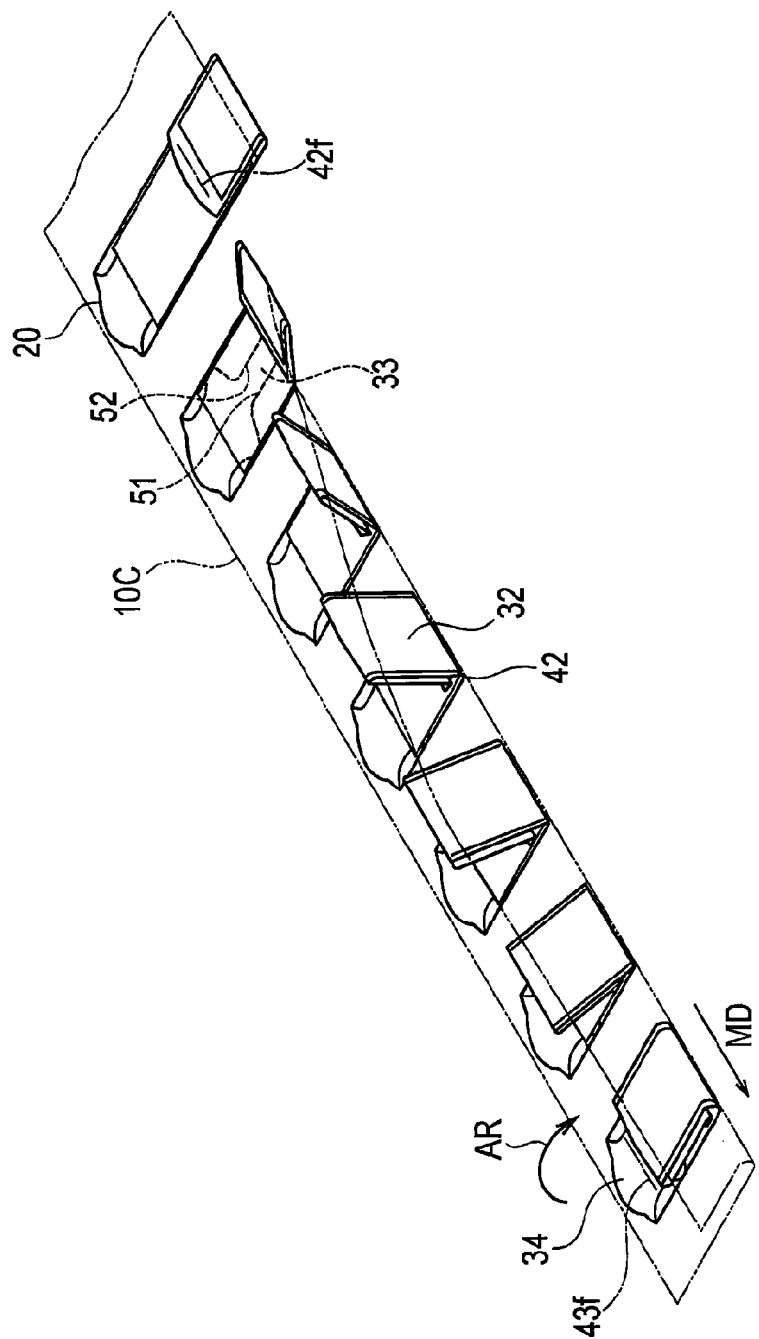
FIG. 10 illustrates changes in shape of the sanitary napkin 20 which is being folded by the folding device 200 according to the embodiment of the present invention.

In the second folding step, the folding device 200 illustrated in FIGS. 8 and 9 is used. The folding device 200 is provided with a sailor plate 220, a folding line creation disc 230 and a pressing roller 240.

The sailor plate 220 abuts the continuous sheet 10C conveyed by the conveyor (not illustrated) and raises the third portion 32 over which the second portion 31 is folded substantially upright with respect to the skin side surface of the fourth portion 33. In particular, the sailor plate 220 has a configuration such that its distance from the pressing roller 240 becomes smaller as it approaches the downstream of the conveyance direction MD. The fourth portion 33 and the fifth portion 34 (see FIG. 9) of the sanitary napkin 20 are pressed down by the pressing roller 240, and the third portion 32 over which the second portion 31 is folded is folded by the sailor plate 220 and the folding line creation disc 230 in a gap formed between the sailor plate 220 and the side surface of the pressing roller 240. In particular, as illustrated in FIGS. 9(a) and 9(b), the first portion 20a is folded by an outer edge of the folding line creation disc 230 to prevent separation of the folded second portion 31 from the third portion 32.

The folding line creation disc 230 is rotated in accordance with the conveyance velocity of the sanitary napkins 20. A peripheral portion of the folding line creation disc 230 is brought into contact with the second folding line 42f of the sanitary napkin 20 while being rotated and forms a folding line in the sanitary napkin 20. In this manner, the second folding portion 42 is formed in the sanitary napkin 20.

(2.2.3) Third Folding Step

As illustrated in FIGS. 4(c) and 4(d), in the third folding step, the fifth portion 34 is folded together with the packaging medium 10 in a direction of arrow AR over the side of the non-skin side surface of the third portion 32 which has been folded over the side of the skin side surface of the fourth portion 33 in the widthwise direction of the sanitary napkin 20 along third folding position 43f located at a boundary of the fourth portion 33 and the fifth portion 34. The fifth portion 34 may be folded by a folding device similar to the folding device 200 used in the second folding step.

In this manner, the fourth portion 34 is folded over the non-skin side surface of the third portion 32, which has been folded over the skin side surface of the fourth portion 33, together with the packaging medium 10 in the third folding portion 43.

As illustrated in FIG. 10, the pair of wings (i.e., the wing 51 and the wing 52) are provided in the fourth portion 33. As illustrated in FIGS. 4(b) and 4(c), the wing release paper 53 includes a joint portion 53a which is joined to a main body release paper 70 located in the second portion 31. The joint portion 53a is located further outward in the lengthwise direction than an outer side end of the wing adhesive portion 51a (the wing adhesive portion 52a) in the lengthwise direction of the sanitary napkin 20.

After the third folding step, the fifth portion 34 folded together with the packaging medium 10 over the side of the non-skin side surface of the third portion 32 is joined to the third portion 32 with the hot-melt adhesive member. The locking tape 15 is then attached.

In the packaged product 1 described above, the length of the packaging medium 10 in the lengthwise direction of the sanitary napkin 20 is shorter than the length of the sanitary napkin 20, and the packaging medium 10 is provided only on the non-skin side surface of the third portion 32, on the non-skin side surface of the fourth portion 33 and on the non-skin side surface of the fifth portion 34.

That is, the packaging medium 10 is not provided on the non-skin side surface of the second portion 31. Accordingly, the amount of the packaging medium 10 required to package the sanitary napkin 20 can be saved and the manufacturing cost can be reduced. If the sanitary napkin 20 is folded into four as described above, the sanitary napkin 20 can be reliably packaged with a reduced amount of the packaging media 10.

FIGS. 9(a) to 9(e) are schematic diagrams of steps S1 to S5 of FIG. 8 seen from the downstream of the conveyance direction.

FIGS. 11(a) to 11(e) illustrate related art steps corresponding to the step S1 to S5 of this embodiment illustrated in FIG. 8. A layer structure of the sanitary napkin 20 is illustrated in a simplified manner in FIGS. 9 and 11.

Figure 11:
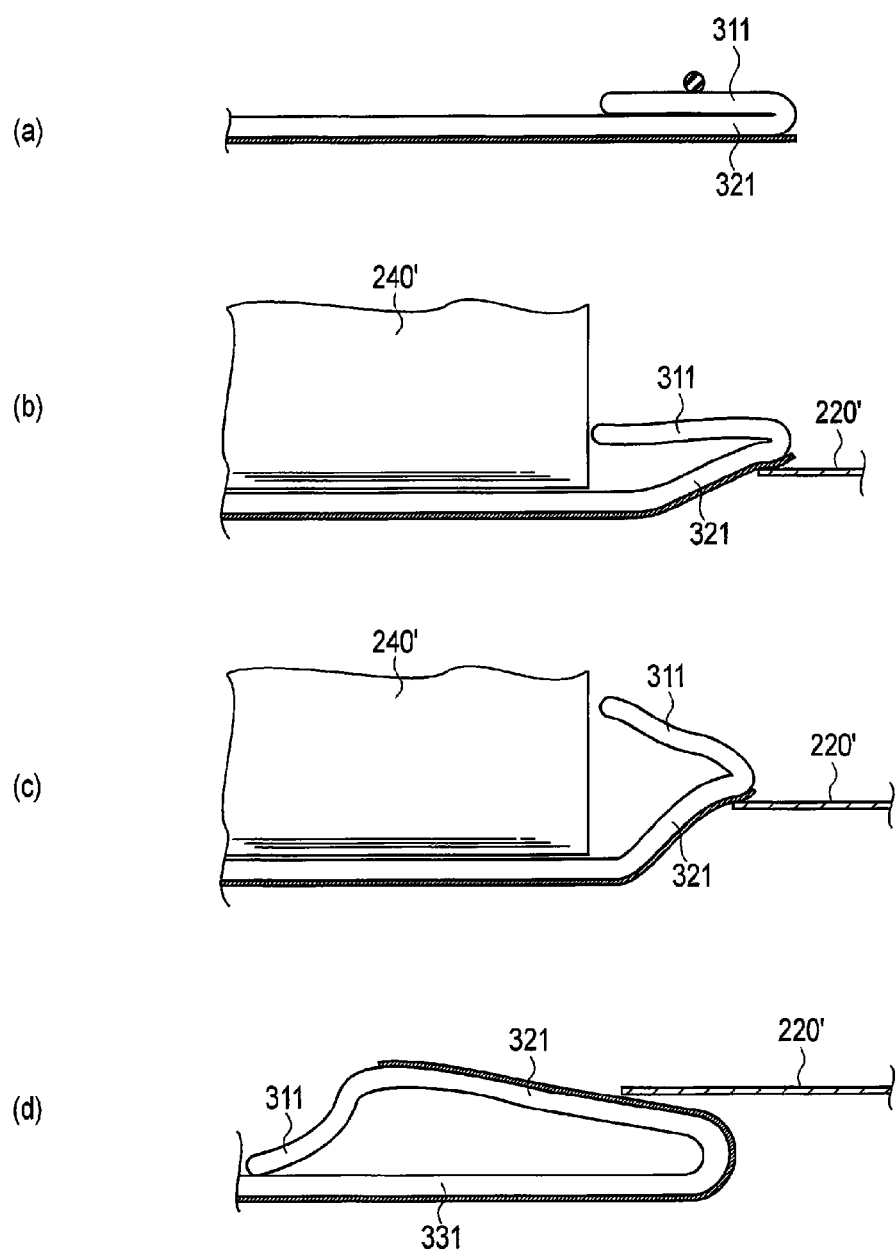
FIGS. 11 (*a*) to 11 (*d*) illustrates deficiencies in related art folding steps.

For example, if the second folding step is performed while the folded end portion 20fe is not caught by the pressing roller 240 in a state in which a second portion 311 is folded over a third portion 321 on the skin side surface of a sanitary napkin 20', a deficiency as schematically illustrated in FIG. 11 may be caused. In particular, since there is no folded end portion 20fe to be caught by the pressing roller 240', when the third portion 321 is folded over a side of a fourth portion 331, the second portion 311 may be separated from the third portion 321 (FIGS. 12(b) and 12(c)). Thus, the sanitary napkin 20' may sometimes be insufficiently folded when the folding step is to be completed.

On the contrary, in the manufacturing steps of the sanitary napkin 20 of this embodiment, the folded end portion 20fe is formed by the first folded portion 44 provided in the side of the first portion 20a of the sanitary napkin 20. With this, even if the packaging medium 10 is not provided on the non-skin side surface of the second portion 31, the folded end portion 20fe is fixed to the skin side surface of the sanitary napkin 20 in the second folding step as illustrated in FIGS. 9(a) and 9(b). It is therefore possible to prevent separation of the second portion 31 from the third portion 32. That is, when the third portion 32 over which the second portion 31 has been folded is folded together with the packaging medium 10 over the side of the skin side surface of the fourth portion 33, the second portion 31 is controlled not to move toward the side of the fourth portion 33. Thus, according to this embodiment, it is possible to prevent insufficient folding of the sanitary napkin 20 when the third portion 32 is folded over the side of the fourth portion 33.

Since the length of the packaging medium 10 is made shorter than the length of the sanitary napkin 20, it is possible to reduce the number of overlapping of the packaging medium 10 when the packaged product 1 is in the state as illustrated in FIG. 4(d). Accordingly, at the time of sealing the end portions of the packaging medium 10, the number of overlapping of the packaging medium 10 is two or three and thus a difference in the number of overlapping of the packaging medium 10 is small. Thus, if the packaging medium 10 is heat sealed with uniform pressure, the deficiency that the packaging medium 10 opens abruptly or that the packaging medium 10 is sealed with excessively high pressure to cause difficulty in opening can be overcome. For example, if the packaging medium 10 is provided on the entire non-skin side surface of the sanitary napkin 20, the number of overlapping of the packaging medium 10 is two in the smallest portion and four in the largest portion. Thus, the above-described deficiency is easily caused.

In this embodiment, the first folding portion 41 located at a boundary of the second portion 31 and the third portion 32 is located further toward the second portion 31 than the center CT in the lengthwise direction of the sanitary napkin 20. With this, the sanitary napkin 20 can be packaged with a reduced amount of the packaging media 10 while being folded into four.

In this embodiment, the wing release paper 53 is joined to the main body release paper 70, and the joint portion 53a is located further outward in the lengthwise direction than an outer side end of the wing adhesive portion 51a (the wing adhesive portion 52a) in the lengthwise direction of the sanitary napkin 20. Thus, as illustrated in FIG. 4(c), when the user holds and pulls up an end portion of the third portion 32 (i.e., a portion of the first folding portion 41) for the development of the packaged product 1, the wing release paper 53 is separated smoothly from the pair of wings. That is, it is not necessary for the user to individually peel off the wing release paper 53, which is useful in attaching the sanitary napkin 20.

In the above-described embodiment, the eight shaped belt mechanism 150 is used in the first folding step. The circular belt 180 which constitutes the eight shaped belt mechanism 150 folds the second portion 31 over the skin side surface of the third portion 32 while in contact with the non-skin side surface of the second portion 31 which has been raised by the folding plate 120. Since the circular belt 180 is rotated in accordance with the conveyance velocity of the sanitary napkin 20, troubles that the second portion 31 is caught by the circular belt 180 can be prevented even if the second portion 31 is conveyed intermittently. If the second portion 31 on which the continuous sheet 10C of the packaging medium 10 has not been provided is folded by the folding device 200 used in the second folding step, it is highly possible that the second portion 31 is caught by the sailor plate 220, which is inconvenient.

(3) Other Embodiments

As described above, while details of the present invention have been disclosed with reference to the embodiments of the present invention, it should not be understood that the discussion and drawings which form a part of the disclosure are restrictive. Various alternatives, examples and operational techniques are obvious for those skilled in the art on the basis of the disclosure.

For example, the embodiments of the present invention can be modified in the following manner. The pair of wings or the pair of hip flaps provided in the sanitary napkin 20 may not necessarily be provided. The widths of the second portion 31, the third portion 32, the fourth portion 33 and the fifth portion 34 are not limited to those of the above-described embodiment but can be changed suitably as long as the sanitary napkin 20 can be folded into four and packaged. Although the sanitary napkin 20 is folded in four, it may alternatively be folded into three.

It is to be understood that the present invention encompasses various other embodiments which are not expressly stated herein. Accordingly, the technical scope of the present invention shall be solely determined by the matter to define the invention relevant to the appended claims that deem to be appropriate in conjunction with the above description.

The entire contents of Japanese Patent Application No. 2011-022625 (filed on Feb. 3, 2010) are incorporated in the present specification by reference.

INDUSTRIAL APPLICABILITY

According to aspects of the present invention, provided is a package structure of an absorbent article in which the absorbent article is packaged reliably while saving a required amount of a packaging medium and a method of manufacturing the package structure.

The invention claimed is:

1. A package structure of an absorbent article which includes the absorbent article and a sheet-like packaging medium which individually packages the absorbent article, the absorbent article having a skin side surface located on a side of a wearer's skin and a non-skin side surface located on a side of underwear of a wearer, the absorbent article having a lengthwise direction and a widthwise direction perpendicular to the lengthwise direction, and the absorbent article and the packaging medium being integrally folded in the lengthwise direction, wherein:
the absorbent article comprises a first portion which includes an end portion of the absorbent article, a second portion which is disposed adjacent to the first portion via a first folded portion, a third portion which is disposed adjacent to the second portion via a second folded portion, a fourth portion which is disposed adjacent to the third portion via a third folded portion and a fifth portion which is disposed adjacent to the fourth portion via a fourth folded portion;
the first portion is folded on a side of a non-skin side surface of the second portion via the first folded portion;
the third portion is folded on a side of a skin side surface of the second portion via the second folded portion;
the fourth portion is folded on the side of the non-skin side surface of the second portion via the third folded portion;
the packaging medium is joined at least partially to the third portion and the fourth portion and not joined to the first portion and the second portion; and
the fifth portion is not folded over the first portion when the absorbent article is folded.

2. The package structure of an absorbent article according to claim 1, wherein:
the absorbent article includes a pair of wings which extend outwardly in the widthwise direction of the absorbent article and are fixed to a crotch portion of the underwear;
the pair of wings include wing adhesive portions formed on a contact surface with the underwear and are folded over the skin side surface of the absorbent article;
the folded pair of wings are integrally provided with a wing release paper, the wing release paper removably attached to the wing adhesive portion of one of the wings and to the wing adhesive portion of the other of the wings, the absorbent article includes a back surface adhesive portion formed on the non-skin side surface;
the back surface is provided with a main body release paper removably attached to the back surface adhesive portion; and
at least a portion of the pair of wings is provided in the fourth portion, and the wing release paper includes a joint portion joined to the main body release paper located in the third portion.

3. The package structure of an absorbent article according to claim 2, wherein the joint portion is located further outward than an outer side end of the wing adhesive portion in the lengthwise direction of the absorbent article.

4. A method of manufacturing a package structure of an absorbent article which includes an absorbent article and a sheet-like packaging medium which individually packages the absorbent article using a device for manufacturing, in which
the absorbent article has a skin side surface located on a side of a wearer's skin and a non-skin side surface located on a side of underwear of a wearer, the absorbent article has a lengthwise direction and a widthwise direction perpendicular to the lengthwise direction, the absorbent article comprises a first portion which includes an end portion of the absorbent article, a second portion which is disposed adjacent to the first portion via a first folded portion, a third portion which is disposed adjacent to the second portion via a second folded portion, a fourth portion which is disposed adjacent to the third portion via a third folded portion and a fifth portion which is disposed adjacent to the fourth portion via a fourth folded portion;

the first portion is folded on a side of a non-skin side surface of the second portion via the first folded portion;

the third portion is folded on a side of a skin side surface of the second portion via the second folded portion;

the fourth portion is folded on the side of the non-skin side surface of the second portion via the third folded portion;

the packaging medium is joined at least partially to the third portion and the fourth portion and not joined to the first portion and the second portion; and the fifth portion is not folded over the first portion when the absorbent article is folded, and the device for manufacturing includes a conveyor which conveys the absorbent article in a conveyance direction and a circular belt provided to come close to the conveyor as it approaches a downstream of the conveyance direction, the method of manufacturing the package structure comprising:

a disposing step in which the absorbent article is disposed on the packaging medium which is successively conveyed by the conveyor in the conveyance direction such that the lengthwise direction of the absorbent article corresponds to a direction perpendicular to the conveyance direction;

a folding step in which one end portion in the lengthwise direction of the absorbent article conveyed together with the packaging medium is brought into contact with a folding plate and thereby folded to be substantially vertical to the conveyance direction and the direction perpendicular to the conveyance direction; and a folding over step in which the one end portion in the lengthwise direction of the absorbent article which has been folded in the folding step is folded on a side of the skin side surface of the absorbent article by bringing the circular belt into contact with the non-skin side surface of the one end portion in the lengthwise direction of the absorbent article.

5. The method of manufacturing the package structure according to claim 4, wherein, in the folding over step, the circular belt is moved from one end portion toward the other end portion in the lengthwise direction of the absorbent article and comes close to the skin side surface of the absorbent article as the circular belt approaches a downstream in the conveyance direction.

* * * * *